US012496208B2

(12) United States Patent
Kang

(10) Patent No.: US 12,496,208 B2
(45) Date of Patent: Dec. 16, 2025

(54) ANKLE ORTHOSIS FOR BED

(71) Applicant: SAMSUNG LIFE PUBLIC WELFARE FOUNDATION, Seoul (KR)

(72) Inventor: Seung Tak Kang, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 291 days.

(21) Appl. No.: 18/256,784

(22) PCT Filed: Dec. 8, 2021

(86) PCT No.: PCT/KR2021/018521
§ 371 (c)(1),
(2) Date: Jun. 9, 2023

(87) PCT Pub. No.: WO2022/124787
PCT Pub. Date: Jun. 16, 2022

(65) Prior Publication Data
US 2024/0024144 A1 Jan. 25, 2024

(30) Foreign Application Priority Data
Dec. 11, 2020 (KR) ........................ 10-2020-0173577

(51) Int. Cl.
*A61F 5/01* (2006.01)

(52) U.S. Cl.
CPC .......... *A61F 5/0116* (2013.01); *A61F 5/0113* (2013.01)

(58) Field of Classification Search
CPC ..... A61F 5/0116; A61F 5/0113; A61F 5/0111; A61F 5/01; A61F 5/048; A61F 13/06; A61F 13/066; A61F 2005/0197
See application file for complete search history.

(56) References Cited

U.S. PATENT DOCUMENTS 5,944,678 A * 8/1999 Hubbard ............... A61F 5/0111 602/65
2009/0192428 A1* 7/2009 DeBoer ................. A61F 13/065 602/65
(Continued)

FOREIGN PATENT DOCUMENTS

CN 106137496 A 11/2016
CN 110313660 A 10/2019
(Continued)

OTHER PUBLICATIONS

International Search Report issued Mar. 16, 2022 in PCT/KR2021/018521 filed on Dec. 8, 2021 2 pages.

*Primary Examiner* — Tarla R Patel
(74) *Attorney, Agent, or Firm* — Oblon, McClelland, Maier & Neustadt, L.L.P.

(57) ABSTRACT

The disclosure relates to an ankle orthosis for a bed. This ankle orthosis for a bed according to an embodiment of the disclosure includes a first support portion having both ends connected to each other to cover a patient's lower body, a second support portion detachably connected to the first support portion, extending from the inside of the first support portion, and covering a patient's sole, and an elastic connection portion detachably connected to the first support portion and the second support portion and including an elastic material, wherein the second support portion is pulled toward a calf side in a state in which one end is arranged on an outer surface of the first support portion on the calf side, and the other end is arranged on a bottom surface of the second support portion.

8 Claims, 8 Drawing Sheets

(56) References Cited

U.S. PATENT DOCUMENTS

| | | | | |
|---|---|---|---|---|
| 2010/0256544 | A1* | 10/2010 | Colon | A61F 5/05 602/28 |
| 2011/0034846 | A1* | 2/2011 | Draper | A61F 5/0111 602/27 |
| 2011/0082403 | A1 | 4/2011 | Hill | |
| 2012/0145167 | A1 | 6/2012 | Davis | |
| 2014/0316321 | A1 | 10/2014 | Mueller et al. | |
| 2017/0165094 | A1 | 6/2017 | Voskuilen et al. | |

FOREIGN PATENT DOCUMENTS

| | | | | | |
|---|---|---|---|---|---|
| EP | 3 139 872 | B1 | | 9/2020 | |
| JP | 11-56940 | A | | 3/1999 | |
| JP | H1156940 | A | * | 3/1999 | |
| JP | 3073408 | U | | 11/2000 | |
| JP | 3149831 | U | | 4/2009 | |
| KR | 10-2020-0025413 | | | 3/2020 | |
| WO | WO-2015170973 | A1 | * | 11/2015 | A61F 5/0111 |
| WO | WO-2018005955 | A1 | * | 1/2018 | A41B 11/00 |
| WO | WO-2022185483 | A1 | * | 9/2022 | A61F 5/0113 |

* cited by examiner

ANKLE ORTHOSIS FOR BED

TECHNICAL FIELD

The disclosure relates to an ankle orthosis, and more particularly, to an ankle orthosis for a bed in which an ankle of a patient may be pulled up and fixed while the patient is lying in the bed.

BACKGROUND ART

Ankle orthoses previously launched are used to assist walking for patients with foot drop, where the ankle droops downward, and are thus made of a hard material in order to support the patient's ankle.

Meanwhile, patients who spend a long time lying in bed experience a phenomenon in which an ankle droops downward, and when the related-art is applied to such patients, injuries or pressure sores may occur when the foot is pressed against an ankle orthosis made of a hard material.

In addition, when the patient is in a supine position, a night splint commonly used for a bed may cause the patient's ankle to turn outward due to a weight of the night splint, causing discomfort to the patient and causing body imbalance. In addition, a portion pressed by the night splint may occur when the patient changes position, such as lying on his or her side.

Accordingly, there is a need for an ankle orthosis suitable for bedridden patients.

The background art described above is technical information that the inventor possessed for derivation of the disclosure or acquired in a process of derivation of the disclosure, and cannot necessarily be said to be known technology disclosed to the general public prior to the filing of the disclosure.

DISCLOSURE

Technical Problem

The disclosure provides an ankle orthosis in which an ankle-drooping phenomenon may be prevented and which has a lightweight structure in close contact with a patient's body so that there is no inconvenience for living in a bed while the patent wears the ankle orthosis.

However, this is only an example, and the objective of the disclosure is not limited thereto.

Technical Solution

An ankle orthosis for a bed according to an embodiment of the disclosure includes a first support portion having both ends connected to each other to cover a patient's lower body, a second support portion detachably connected to the first support portion, extending from the inside of the first support portion, and covering a patient's sole, and an elastic connection portion detachably connected to the first support portion and the second support portion and including an elastic material, wherein the second support portion is pulled toward a calf in a state in which one end is arranged on an outer surface of the first support portion on a calf side, and the other end is arranged on a bottom surface of the second support portion.

In the ankle orthosis for a bed according to an embodiment of the disclosure, the first support portion may be arranged to cover a patient's ankle from a patient's calf, and the second support portion may be arranged inside the first support portion and covers the patient's ankle and sole without covering a patient's instep.

In the ankle orthosis for a bed according to an embodiment of the disclosure, the second support portion may change a location connected to the first support portion through a fastening member arranged at one side and adjust a length by which the patient's sole is covered.

In the ankle orthosis for a bed according to an embodiment of the disclosure, the elastic connection portion may be provided in plural, and the plurality of elastic connection portions may be arranged to be spaced apart from each other in a longitudinal direction on the bottom surface of the second support portion, and may pull the patient's sole toward the calf at different locations.

In the ankle orthosis for a bed according to an embodiment of the disclosure, the elastic connection portion may include a forefoot connector located at one side of the bottom surface of the second support portion, and a midfoot connector located on another side of the bottom surface of the second support portion.

In the ankle orthosis for a bed according to an embodiment of the disclosure, the forefoot connector may have one end arranged in a first half in a longitudinal direction of the bottom surface of the second support portion, and have another end arranged on the outer surface of the first support portion on the calf side, and the midfoot connector may have one end arranged to include a center of the bottom surface of the second support portion in the longitudinal direction, and have another end arranged on the outer surface of the first support portion on the calf side.

In the ankle orthosis for a bed according to an embodiment of the disclosure, the forefoot connector may be provided in plural, and an area of one end arranged in the first half may be larger than an area of the other end.

In the ankle orthosis for a bed according to an embodiment of the disclosure, the forefoot connector may have a larger area for supporting the second support portion than the midfoot connector.

In the ankle orthosis for a bed according to an embodiment of the disclosure, the other end of the midfoot connector may be located higher than the other end of the forefoot connector in the first support portion.

In the ankle orthosis for a bed according to an embodiment of the disclosure, the elastic connection portion may change a location connected to the first support portion through a second fastening member arranged at one side.

Other aspects, features, and advantages other than those described above will become clear from the detailed description, claims, and drawings for carrying out the disclosure below.

Advantageous Effects

An ankle orthosis for a bed according to an embodiment of the disclosure is for a patient who spends a long time in bed, and an elastic connection may pull the forefoot of the foot to prevent an ankle of the patient from drooping downward.

In an ankle orthosis for a bed according to an embodiment of the disclosure, because the elastic connector supports and pulls the sole of the foot in a wide area at various positions, the patient's ankle may be pulled and supported more easily.

An ankle orthosis for a bed according to an embodiment of the disclosure has a simple and lightweight structure and may be in contact with the patient's skin for a long period of time.

An ankle orthosis for a bed according to an embodiment of the disclosure does not cover the patient's instep, and thus, it is easy to treat or nurse the patient, such as giving an injection or inserting a catheter in the patient's instep.

BEST MODE

Figure 1:
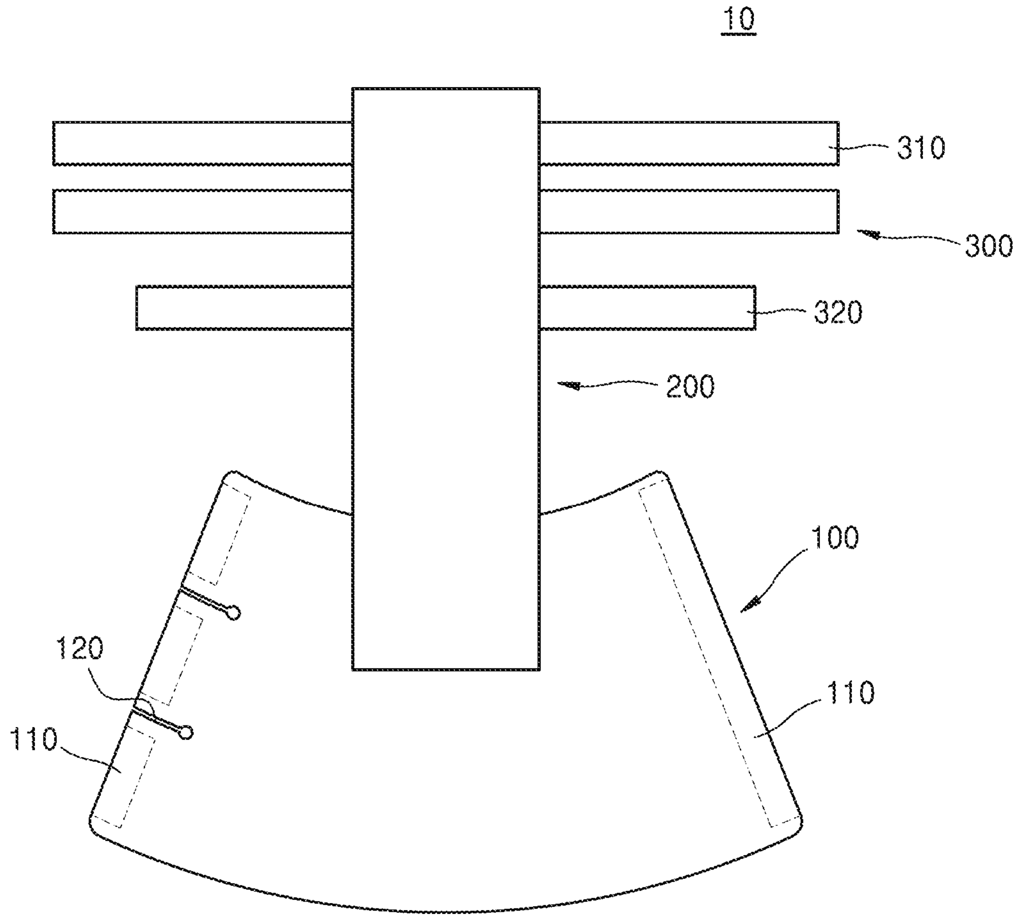
FIG. 1 illustrates an ankle orthosis for a bed according to an embodiment of the disclosure.

An ankle orthosis for a bed according to an embodiment of the disclosure includes a first support portion having both ends connected to each other to cover a patient's lower body, a second support portion detachably connected to the first support portion, extending from the inside of the first support portion, and covering a patient's sole, and an elastic connection portion detachably connected to the first support portion and the second support portion and including an elastic material, wherein the second support portion is pulled toward a calf in a state in which one end is arranged on an outer surface of the first support portion on a calf side, and the other end is arranged on a bottom surface of the second support portion.

MODE FOR INVENTION

As the disclosure allows for various changes and numerous embodiments, certain embodiments will be illustrated in the drawings and described in detail in the written description. However, this is not intended to limit the disclosure to specific embodiments, and should be understood to include all conversions, equivalents, and substitutes included in the spirit and scope of the disclosure. In the description of the disclosure, even when shown in different embodiments, the same identification characters are used for the same elements.

One or more embodiments of the disclosure will be described below in more detail with reference to the accompanying drawings. Those elements that are the same or are in correspondence are rendered the same reference numeral regardless of the figure number, and redundant descriptions thereof are omitted.

In an embodiment below, terms such as "first" and "second" are used herein merely to describe a variety of elements, but the elements are not limited by the terms. Such terms are used only for the purpose of distinguishing one element from another element.

In an embodiment below, an expression used in the singular encompasses the expression of the plural, unless it has a clearly different meaning in the context.

In an embodiment below, term such as "include" or "comprise" may be construed to denote a certain characteristic or constituent element, or a combination thereof, but may not be construed to exclude the existence of or a possibility of addition of one or more other characteristics, elements, or combinations thereof.

Sizes of elements in the drawings may be exaggerated or reduced for convenience of explanation. In other words, since sizes and thicknesses of elements in the drawings are arbitrarily illustrated for convenience of explanation, the following embodiments are not limited thereto.

In the following embodiments, the x-axis, the y-axis, and the z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

When a certain embodiment may be implemented differently, a specific process order may be performed differently from the described order. For example, two consecutively described processes may be performed substantially at the same time or performed in an order opposite to the described order.

Terms used in the disclosure are only used to describe specific embodiments, and are not intended to limit the disclosure. It should be understood that terms, such as "comprise", "include", or "have", used in the detailed description are intended to designate the presence of a feature, number, operation, action, element, component, or a combination thereof described in the description of the disclosure, and do not preclude the existence or addition of one or more other features, numbers, operations, actions, elements, components, or combinations thereof.

Figure 2:
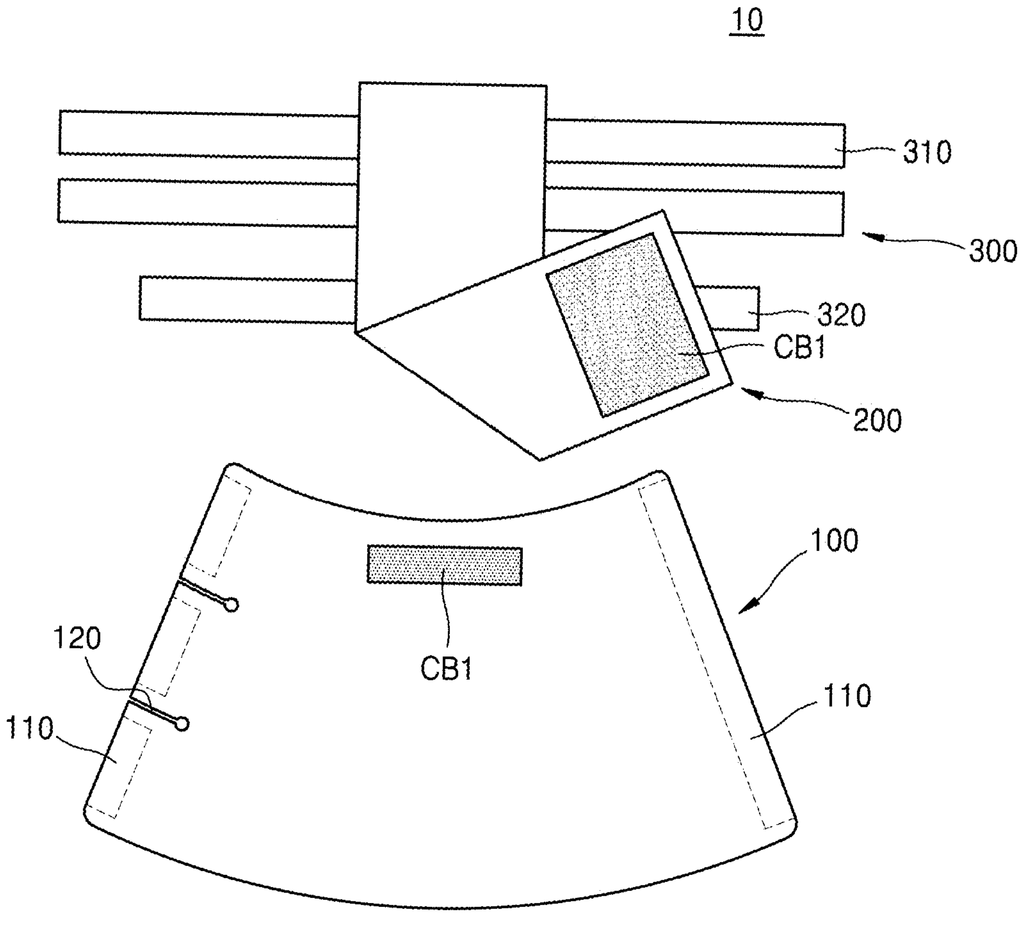
FIGS. 2 and 3 illustrate a state in which locations of a first support portion and a second support portion are adjusted, according to an embodiment of the disclosure.
Figure 3:
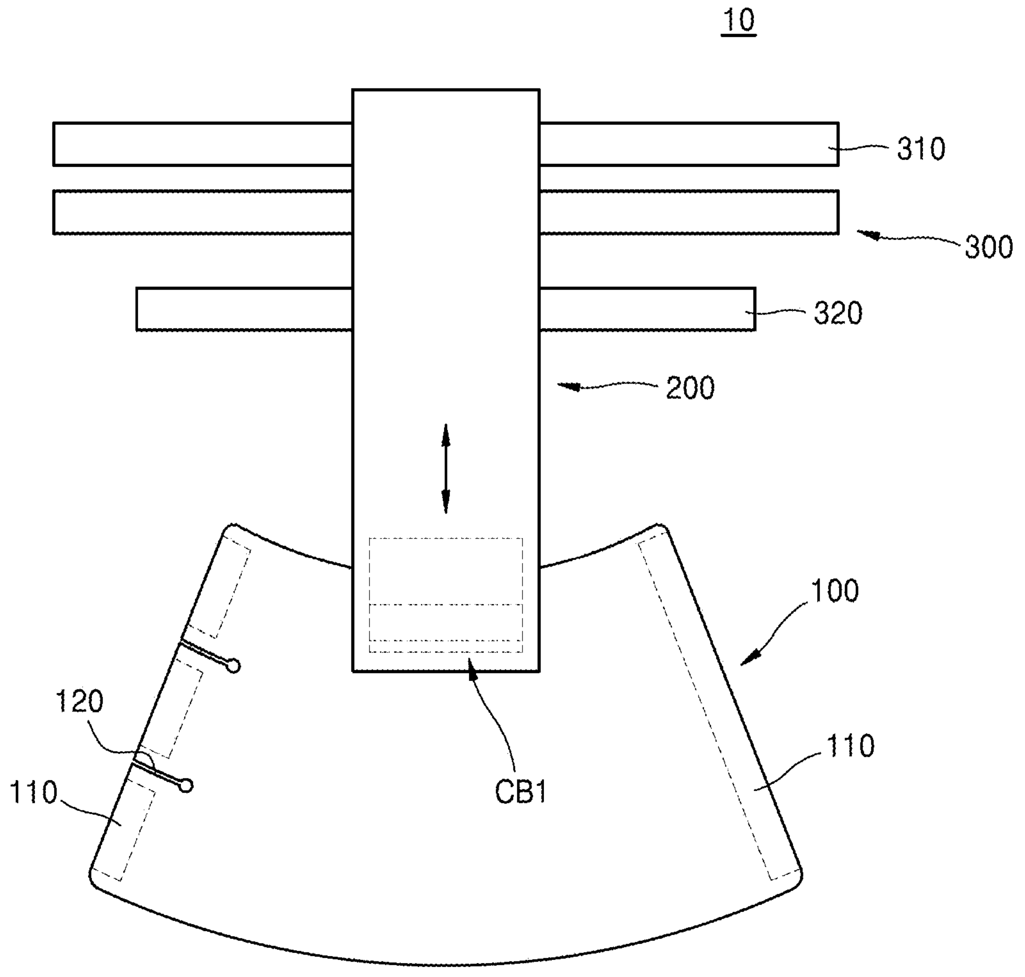
Figure 4:
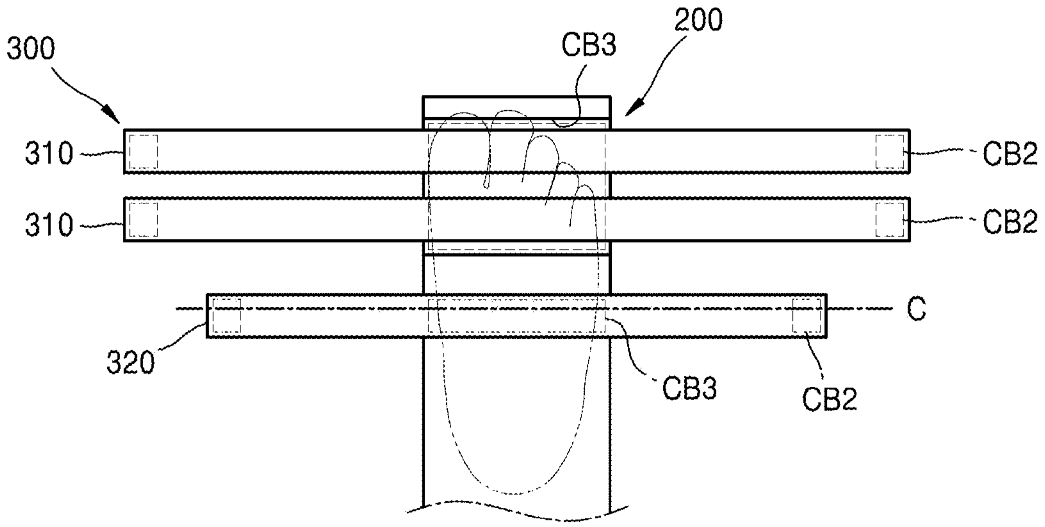
FIG. 4 illustrates a bottom surface of the second support portion according to an embodiment of the disclosure.
Figure 5:
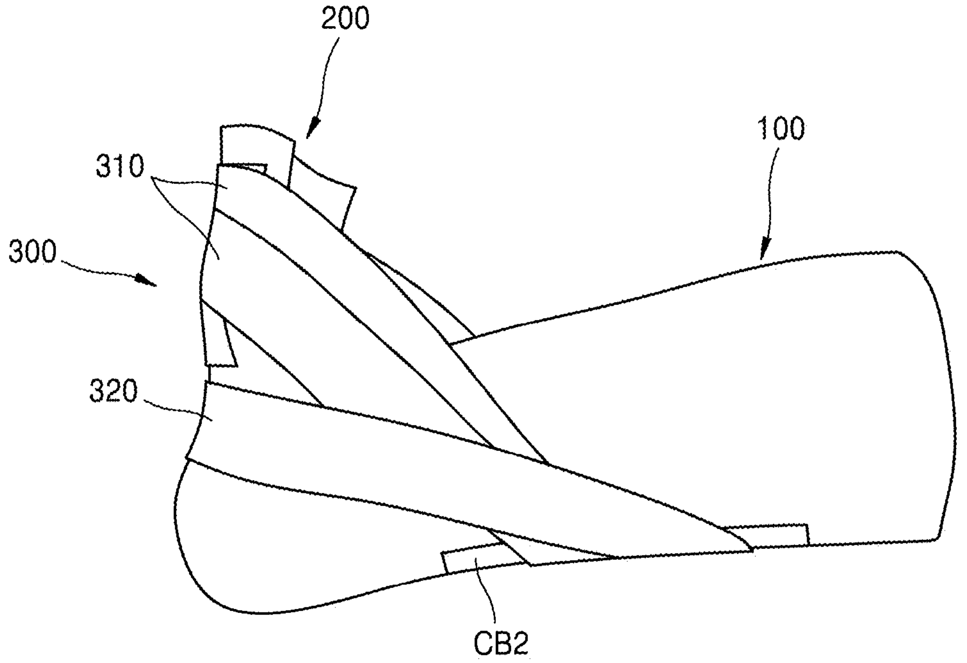
FIG. 5 illustrates a state in which a location of an elastic connection portion is adjusted, according to an embodiment of the disclosure.
Figure 6A:
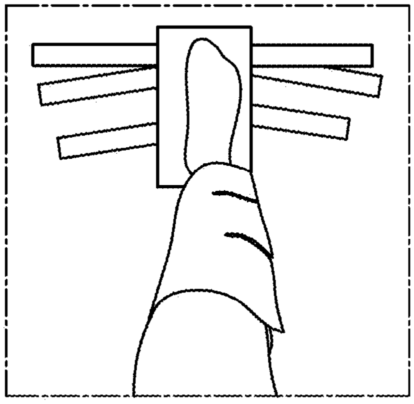
FIGS. 6A, 6B, and 6C illustrate an order of putting on an ankle orthosis for a bed.
Figure 6B:
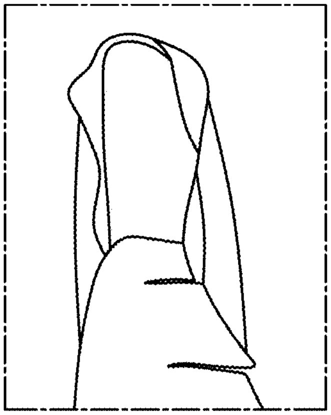
Figure 6C:
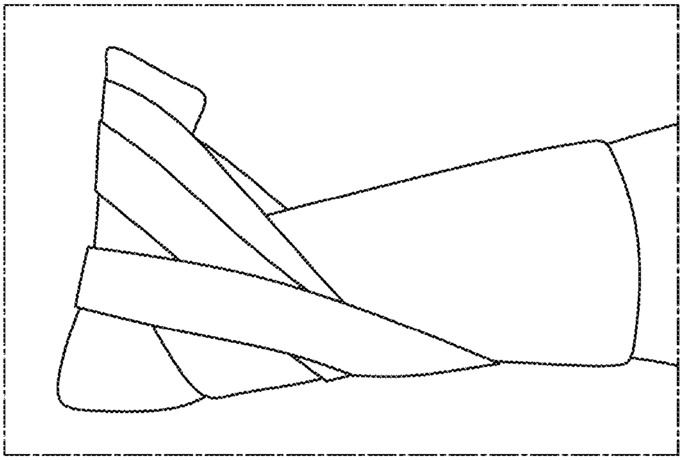

FIG. 1 illustrates an ankle orthosis 10 for a bed according to an embodiment of the disclosure, FIGS. 2 and 3 illustrate a state in which locations of a first support portion 100 and a second support portion 100 are adjusted, according to an embodiment of the disclosure, FIG. 4 illustrates a bottom surface of the second support portion 200 according to an embodiment of the disclosure, FIG. 5 illustrates a state in which a location of an elastic connection portion 300 is adjusted, according to an embodiment of the disclosure, and FIGS. 6A, 6B, and 6C illustrate an order of putting on the ankle orthosis 10 for a bed, according to an embodiment of the disclosure.

The ankle orthosis 10 for a bed according to an embodiment of the disclosure may be applied to patients living in bed with an ankle injury. The ankle orthosis 10 for a bed may be used to support ankles of patients who have difficulty moving the lower body, such as patients with foot drop, or patients who live a long life in bed due to other chronic diseases.

Referring to FIGS. 1 to 5, the ankle orthosis 10 for a bed according to an embodiment of the disclosure may include the first support portion 100, the second support portion 200, and the elastic connection portion 300.

The first support portion 100 is a member that surrounds the patient's lower body and is connected to the second support portion 200 through the elastic connection portion 300 to be described later, fixing a state in which the sole of the patients' foot is pulled. For example, as shown in FIG. 1, the first support portion 100 may, in an unfolded state, have a truncated cone shape or a rectangular shape, or opposite ends may be connected to each other in a width direction. To this end, the first support portion 100 may have a fixing member 110, such as Velcro, belts, buttons, or magnets, at the opposite ends in the width direction.

In an embodiment, the first support portion 100 may have a plurality of incision grooves 120 formed at one end in the width direction. In more detail, as shown in FIG. 1, a plurality of incision grooves 120 may be arranged to be spaced apart from each other in a longitudinal direction at the one end of the first support portion 100 in the width direction. Accordingly, a movable range of the first support portion 100 arranged at opposite sides of the incision groove 120 increases, and the first support portion 100 may be arranged to overlap each other or spaced apart from each other. Accordingly, the first support portion 100 may be appropriately arranged in consideration of the patient's body shape or condition.

In an embodiment, the first support portion 100 may have one end covering the patient's ankle in the longitudinal direction, and the other end covering under the patient's knee. Accordingly, the first support portion 100 may cover the patient's calf and ankle in a state in which opposite ends are fastened in the width direction. A related-art ankle orthosis includes a hard material to assist walking or prevent a shock, and is configured to cover only a portion of an ankle or a calf. On the other hand, the first support portion 100 according to an embodiment entirely covers the calf of the patient to distribute pressure applied to the ankle and the calf.

The second support portion 200 prevents the patient's ankle from drooping downward by covering a patient's sole and pulling the patient's sole toward the calf. For example, the second support portion 200 may be detachably connected to the first support portion 100, and may extend from the inside of the first support portion 100 and cover the sole of the patient. However, the second support portion 200 is not necessarily coupled or connected only to the first support portion 100, and may be detachably connected to other support portion not shown.

In an embodiment, the first support portion 100 and the second support 200 may each include a first fastening member CB1. For example, the first fastening member CB1 may be arranged at one side of the inner surface of the first support portion 100 or one end of the second support portion 200. A type of the first fastening member CB1 is not particularly limited, and may be Velcro, a belt, a button, or a magnet. For convenience of description, a case in which the first fastening member CB1 is Velcro is mainly described below.

In an embodiment, the first fastening member CB1 may be elongated in the longitudinal direction. In more detail, as shown in FIG. 2, the first fastening member CB1 arranged in the second support portion 200 may be elongated in the longitudinal direction to change a fastening position with the first fastening member CB1 arranged in the first support portion 100.

Accordingly, as shown in FIG. 3, a length of the second support portion 200 extending from the inside of the first support portion 100 and protruding outward may be adjusted. Through this, in the ankle orthosis 10 for a bed according to an embodiment of the disclosure, an area in which the second support portion 200 covers the sole of the patient may be adjusted according to the patient's body shape or condition. In FIG. 2, the first fastening member CB1 arranged in the second support portion 200 is elongated. However, the disclosure is not limited thereto. The first fastening member CB1 arranged in the first support portion 100 may also be elongated in the longitudinal direction.

In an embodiment, the second support portion 200 may not cover the instep of the patient. For example, as shown in FIG. 4, in a state in which the second support portion 200 covers a foot of the patient, the second support portion 200 may be arranged to cover the patient's ankle, sole, or side of the foot without covering the instep.

In more detail, a related-art ankle orthosis is configured to cover up to the instep of the patient for walking assistance or impact protection. However, there may be a case in which an injection may be given through the instep or an intravenous catheter may need to be inserted depending on the patient's condition. Because the related-art ankle orthosis is configured to cover the entire instep, there is a hassle of dismantling the ankle orthosis every time an injection is given or an intravenous catheter is inserted.

The ankle orthosis 10 for a bed according to an embodiment of the disclosure is configured such that the second support portion 200 does not cover the patient's instep while sufficiently supporting the patient's sole, and thus, it is easier and quicker to administer an injection or insert an intravenous catheter.

In another embodiment, the second support portion 200 may be connected in the width direction and may have an insertion groove (not shown) on the upper surface thereof. In other words, the second support portion 200 has the insertion groove on the upper surface thereof and entirely covers the foot of the patient, so that an injection or an intravenous catheter may be inserted through the insertion groove.

The elastic connection portion 300 is connected to the first support portion 100 and the second support portion 200 and pull the second support portion 200 toward the patient's calf. For example, the elastic connection portion 300, which is a band-shaped member having a predetermined area, is detachably connected to the first support portion 100 and the second support portion 200 and may include an elastic material so as to pull the second support portion 200 toward the calf in a state in which one end of the elastic connection portion 300 is arranged on an outer surface on the calf side, and the other end is arranged on the bottom surface of the second support portion 200.

In an embodiment, the elastic connection portion 300 is provided in plural and may be arranged to be spaced apart from each other in the longitudinal direction on the bottom surface of the second support portion 200 so as to pull the patient's sole toward the calf in different locations.

In more detail, as shown in FIG. 4, the second support portion 200 is arranged under the patient's sole, and the elastic connection portion 300 may be arranged on the bottom surface of the second support portion 200. In addition, the elastic connection portion 300 may include a forefoot connector 310 and a midfoot connector 320.

The forefoot connector 310 and the midfoot connector 320 may be respectively arranged at one side and the other side of the bottom surface of the second support portion 200. For example, the forefoot connector 310 may have one end arranged in the first half of the bottom surface of the second support portion 200 based on a center C in the longitudinal direction. In addition, the midfoot connector 320 may be arranged to include the center C in the longitudinal direction of the bottom surface of the second support portion 200. Here, the second support portion 200 may protrude from the inside of the first support portion 100 to the outside and correspond to a portion covering the patent's sole. Accordingly, the ankle orthosis 10 for a bed according to an embodiment of the disclosure may fix a patient's forefoot and midfoot in a state in which the patient's forefoot and midfoot are both pulled.

In more detail, in the related-art ankle orthosis, a member for pulling a portion covering a patient's foot is biased to one side of the instep or the sole. Due to the above, while pulling the foot, the foot twists or the forefoot cannot be pulled uniformly.

The ankle orthosis 10 for a bed according to an embodiment of the disclosure has a plurality of elastic connection portions 300 and evenly supports and pulls the forefoot and the midfoot of the patient, so that the patient's foot may be uniformly pulled and fixed.

In an embodiment, the other end of the forefoot connector 310 may be arranged at an outer surface of the first support portion 100 on the calf side. In addition, the other end of the midfoot connector 320 is arranged on the outer surface of the first support portion 100 on the calf side and may be arranged higher than the other end of the forefoot connector 310. Through the above, the midfoot connector located on the inside of the sole compared to the forefoot connector 310 may be more stably connected to the first support portion 100.

In an embodiment, the forefoot connector 310 is provided in plural, and an area of one end arranged in the first half of the patient's sole may be larger than an area of the other end. In more detail, as shown in FIG. 4, the forefoot connector 310 includes a pair of bands, and to entirely cover the forefoot, an area of one end connected to the second support portion 200 may be larger than an area of the other end.

In an embodiment, the plurality of forefoot connectors 310 may share one area connected to the second support portion 200.

In FIG. 4, it is shown that the forefoot connector 310 includes a pair, i.e., two bands. However, the number thereof is not particularly limited.

In an embodiment, an area in which the forefoot connector 310 supports the second support portion 200 may be larger than an area in which the midfoot connector 320 supports the second support portion. Accordingly, in a state in which the elastic connection portion 300 is connected to the first support portion 100 and the second support portion 200, the forefoot may be pulled more stably and uniformly.

In an embodiment, the elastic connection portion 300 may be detachably connected to the first support portion 100 through a second fastening portion CB2. For example, as shown in FIG. 5, the first support portion 100 has the second fastening portion CB2 on the outer surface thereof, and the elastic connection portion 300 may have a second fastening member CB2 corresponding thereto, at the other end thereof. In a state in which one end of the elastic connection portion 300 is connected to the second support portion 200, the elastic connection portion 300 may have the other end fastened to the first support portion 100 so as to pull the second support portion 200 toward the calf. A type of the second fastening portion CB2 is not particularly limited, and may be Velcro, a belt, a button, or a magnet.

In an embodiment, the elastic connection portion 300 may change a location connected to the first support portion 100 through the second fastening member CB2. For example, as shown in FIG. 5, the second fastening member CB2 may be broadly formed in a longitudinal direction and a circumferential direction on the outer surface of the first support portion 100. Accordingly, the location of the elastic connection portion 300 may be adjusted by fastening the second fastening portion arranged at the other end of the elastic connection portion 300 to a specific location of the second fastening member CB2 in the first support portion 100.

In FIG. 5, a portion of the second fastening member CB2 is formed on the calf side. However, the disclosure is not limited thereto. For example, the second fastening member CB2 may also be formed on a side or a front surface (shin side) of the first support portion 100. Alternatively, the second fastening member CB2 may be formed on an entire surface of the first support portion 100 exposed to the outside in a state in which the first support portion 100 covers the patient's calf. Accordingly, a location at which the elastic connection portion 300 is connected and fixed to the first support portion 100 may be adjusted in consideration of the patient's body shape and condition.

In an embodiment, the elastic connection portion 300 may be detachably connected to the second support portion 200 through a third fastening member CB3. For example, as shown in FIG. 4, the second support portion 200 has the third fastening member CB3 on the bottom surface thereof, and the elastic connection portion 300 may have a third fastening member CB3 corresponding thereto, at one end thereof. A type of the third fastening member CB3 of the elastic connection portion 300 is not particularly limited, and may be Velcro, a belt, a button, or a magnet.

In an embodiment, the elastic connection portion 300 may change a location connected to the second support portion 200, through the third fastening member CB3. For example, as shown in FIG. 4, the third fastening member CB3 may be broadly formed on the bottom surface of the second support portion 200. Accordingly, the third fastening member CB3 arranged at the other end of the elastic connection portion 300 may be fastened to a specific location of the third fastening member CB3 of the second support portion 200, to adjust a location of the elastic connection portion 300.

In FIG. 4, the third fastening member CB3 is formed on a partial surface of the second support portion 200, and the third fastening members CB3 connected to the forefoot connector 310 and the midfoot connector 320 are separated from each other. However, the disclosure is not limited thereto. For example, the third fastening member CB3 may be arranged across the entire bottom surface of the second support portion 200. In addition, the third fastening member CB3 connected to the forefoot connector 310 and the midfoot connector 320 may be integrally formed as a single body. Accordingly, a location at which the elastic connection portion 300 is connected and fixed to the second support portion 200 may be adjusted in consideration of the patient's body shape and condition.

A state of putting on the ankle orthosis 10 for a bed according to an embodiment of the disclosure is described below with reference to FIGS. 6A, 6B, and 6C.

First, as shown in FIG. 6A, the ankle orthosis 10 for a bed is put on so that the first support portion 100 covers the patient's lower body. In this case, one end is arranged under the knee, and the other end is arranged at the ankle so that the first support portion 100 entirely covers the patient's calf. Here, the second support portion 200 may be in a state of being connected to the inside of the first support portion 100 through the first fastening member CB1. A location of the second support portion 200 may be appropriately adjusted in consideration of the patient's body shape and condition. In addition, one end of the elastic connection portion 300 may be in a state of being connected to the bottom surface of the second support portion 200 through the third fastening member CB3. A location of the elastic connection portion 300 with respect to the second support portion 200 may be appropriately adjusted in consideration of the patient's body shape and condition.

Next, as shown in FIG. 6B, the other end of the elastic connection portion 300 is fastened with the first support portion 100 through the second fastening member CB2.

Next, as shown in FIG. 6C, in a state in which the elastic connection portion 300 connects the first support portion 100 and the second support portion 200, a location of the elastic connection portion 300 is adjusted to sufficiently pull the patient's sole, more specifically, forefoot, toward the calf. A location of the elastic connection portion 300 with respect to the first support portion 100 may be adjusted by adjusting a location of the second fastening member CB2 in consideration of the patient's body shape and condition.

In an embodiment, the ankle orthosis 10 for a bed according to the disclosure may include a fabric material. The ankle orthosis 10 for a bed is in contact with the patient's skin for a long period of time and pressed by a patient's body weight, and thus, the first support portion 100, the second support portion 200, and the elastic connection portion 300 may all include a fabric material so that an allergic reaction may be minimized. In addition, the ankle orthosis 10 for a bed is light in weight, simpler in configuration, and more economical compared to the related-art ankle orthosis including a hard material.

The ankle orthosis 10 for a bed according to an embodiment of the disclosure is for patients living in bed for a long time, and the elastic connection portion 300 pulls the forefoot so as to prevent the patient's ankle from drooping downward.

Because the elastic connection portion 300 supports and pulls the sole in various positions and over a wide area, the ankle orthosis 10 for a bed according to an embodiment of the disclosure may pull and support the patient's ankle more easily.

The ankle orthosis 10 for a bed according to an embodiment of the disclosure is simple in configuration and light in weight and may be in contact with the patient's skin for a long period of time.

Because the ankle orthosis 10 for a bed according to an embodiment of the disclosure does not cover the patient's instep, it is easy to treat or nurse a patient by giving an injection or inserting a catheter in the patient's foot.

As described above, the disclosure is described with reference to the embodiments shown in the drawings, but this is only an example. A person of ordinary skill in the art may fully understand that various modifications and other equivalent embodiments are possible from the embodiments. Therefore, the true technical protection scope of the disclosure should be determined based on the appended claims.

Specific technical details described in the embodiments are examples, and do not limit the technical scope of the embodiments. In order to briefly and clearly describe the description of the disclosure, descriptions of related-art general techniques and configurations may be omitted. In addition, a connection of lines between elements shown in the drawings or a connection member exemplarily represent functional connections and/or physical or circuit connections, and may be expressed as various alternative or additional functional connections, physical connections, or circuit connections in actual devices. In addition, unless specifically stated, such as "essential" or "important", elements may not be essential for the application of the disclosure.

The term "the" or similar designations described in the detailed description and claims of the disclosure may refer to both singular and plural, unless otherwise specifically limited. In addition, when a range is described in an embodiment, the disclosure includes embodiments in which an individual value belonging to the range is applied (unless otherwise stated), and is the same as if each individual value included in the range is described in the detailed description of the disclosure. Operations for describing a method according to the disclosure may be performed in a suitable order unless the context clearly dictates otherwise. Embodiments are not necessarily limited according to an order of descriptions of the operations. The use of all examples or illustrative terms in the embodiment is simply for explaining the embodiment in detail, and the scope of the embodiment is not limited due to the examples or illustrative terms unless it is limited by the claims. In addition, one of ordinary skill in the art would appreciate that various modifications, combinations, and changes may be made according to design conditions and factors within the scope of the appended claims or equivalents thereof.

INDUSTRIAL APPLICABILITY

The disclosure may be used in industries related to ankle orthoses for a bed.

The invention claimed is:

1. An ankle orthosis for a bed, the ankle orthosis comprising:

a first support portion having both ends connected to each other to cover a patient's lower body;

a second support portion detachably connected to the first support portion, extending from the inside of the first support portion, and covering a patient's sole; and an elastic connection portion detachably connected to the first support portion and the second support portion and including an elastic material, wherein the second support portion is pulled toward a calf in a state in which one end is arranged on an outer surface of the first support portion on a calf side, and the other end is arranged on a bottom surface of the second support portion, wherein the elastic connection portion comprises:

a forefoot connector located at one side of the bottom surface of the second support portion; and a midfoot connector located on another side of the bottom surface of the second support portion, wherein the forefoot connector has one end arranged in a first half in a longitudinal direction of the bottom surface of the second support portion, and has another end arranged on the outer surface of the first support portion on the calf side, and wherein the midfoot connector has one end arranged to include a center of the bottom surface of the second support portion in the longitudinal direction, and has another end arranged on the outer surface of the first support portion on the calf side.

2. The ankle orthosis for the bed of claim 1, wherein the first support portion is arranged to cover a patient's ankle from a patient's calf, and the second support portion is arranged inside the first support portion and covers the patient's ankle and sole without covering a patient's instep.

3. The ankle orthosis for the bed of claim 1, wherein the second support portion changes a location connected to the first support portion through a fastening member arranged at one side and adjusts a length by which the patient's sole is covered.

4. The ankle orthosis for the bed of claim 1, wherein the elastic connection portion is provided in plural, and the plurality of elastic connection portions are arranged to be spaced apart from each other in a longitudinal direction on the bottom surface of the second support portion, and pull the patient's sole toward the calf side at different locations.

5. The ankle orthosis for the bed of claim 1, wherein the forefoot connector is provided in plural, and an area of one end arranged in the first half is larger than an area of the other end.

6. The ankle orthosis for the bed of claim 1, wherein the forefoot connector has a larger area for supporting the second support portion than the midfoot connector.

7. The ankle orthosis for the bed of claim 1, wherein the other end of the midfoot connector is located higher than the other end of the forefoot connector in the first support portion.

8. The ankle orthosis for the bed of claim 1, wherein the elastic connection portion changes a location connected to the first support portion through a second fastening member arranged at one side.

* * * * *